(12) United States Patent
Renberg

(10) Patent No.: US 7,906,197 B2
(45) Date of Patent: Mar. 15, 2011

(54) FORMABLE LAMINATE OF ANY CIRCUMFERENCE

(76) Inventor: Bo Renberg, Kewanee, IL (US)

( * ) Notice: Subject to any disclaimer, the term of this patent is extended or adjusted under 35 U.S.C. 154(b) by 229 days.

(21) Appl. No.: 10/549,029

(22) PCT Filed: Mar. 17, 2004

(86) PCT No.: PCT/SE2004/000376
§ 371 (c)(1),
(2), (4) Date: Nov. 7, 2006

(87) PCT Pub. No.: WO2004/082544
PCT Pub. Date: Sep. 30, 2004

(65) Prior Publication Data
US 2007/0116935 A1    May 24, 2007

(30) Foreign Application Priority Data
Mar. 18, 2003 (SE) .......................... 0300743

(51) Int. Cl.
*B32B 1/04* (2006.01)
*B32B 3/02* (2006.01)
*B32B 3/12* (2006.01)

(52) U.S. Cl. ............. 428/174; 428/69; 428/72; 428/178
(58) Field of Classification Search .................. 428/174, 428/178, 72, 69; 128/845, 846, 865, 877, 128/DIG. 15, DIG. 20; 5/625, 913; 602/13, 602/6
See application file for complete search history.

(56) References Cited

U.S. PATENT DOCUMENTS 6,254,959 B1 * 7/2001 Hirano et al. .................. 428/71
6,918,393 B2 * 7/2005 Rugfelt et al. ................ 128/845

FOREIGN PATENT DOCUMENTS

GB 2074941 A * 11/1981
WO WO 01/30280 A1 * 5/2001

* cited by examiner

*Primary Examiner* — Jennifer C McNeil
*Assistant Examiner* — Catherine Simone
(74) *Attorney, Agent, or Firm* — Dennison, Schultz & MacDonald

(57) ABSTRACT

As a rule, once they have been fixed in the correct position, fractured bones are supported by a plastic of Paris dressing. Such a dressing is messy and takes time to set. The present invention uses a formable laminate to create a dressing that can rapidly be placed around an injury, said dressing becoming rigid on the setting up of an internal vacuum.

14 Claims, 3 Drawing Sheets

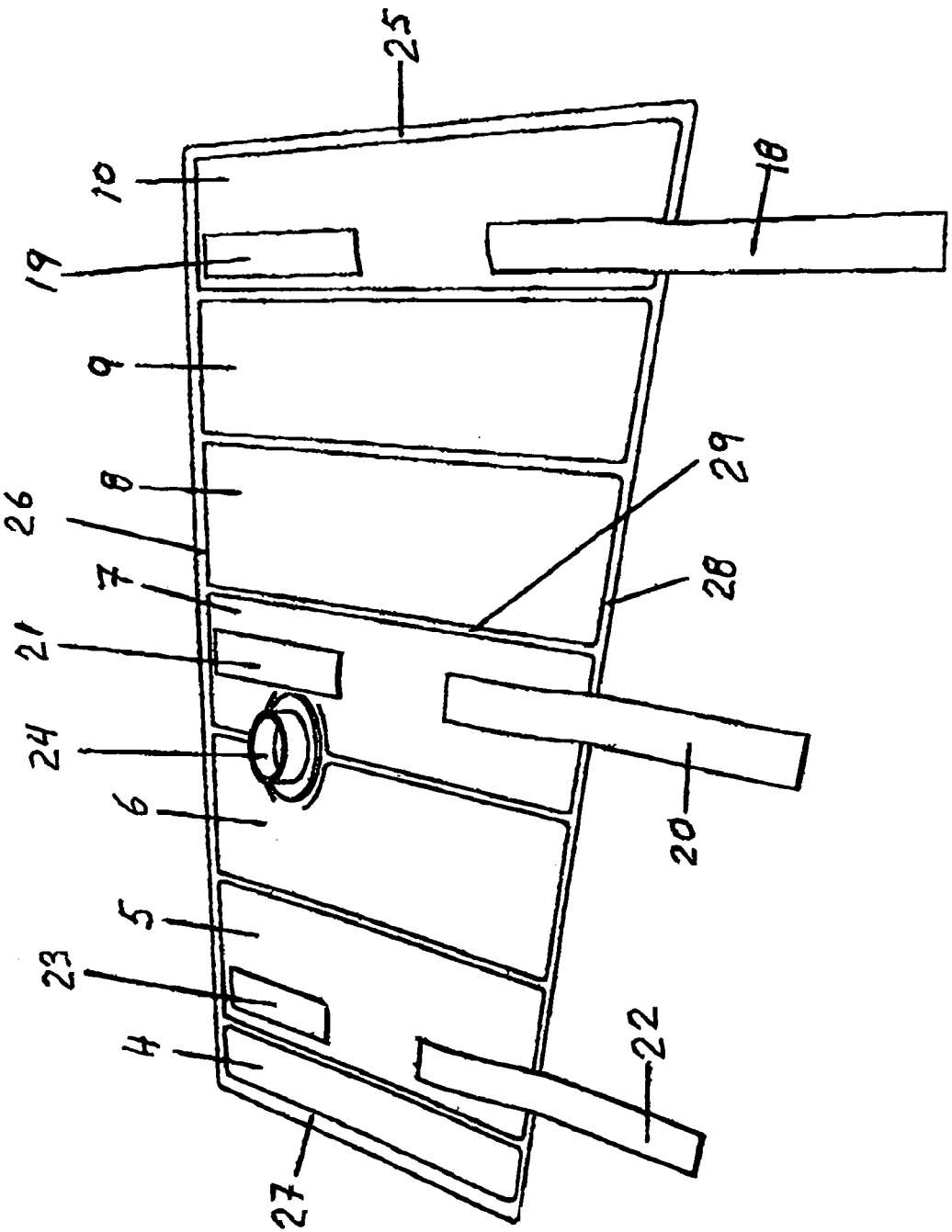

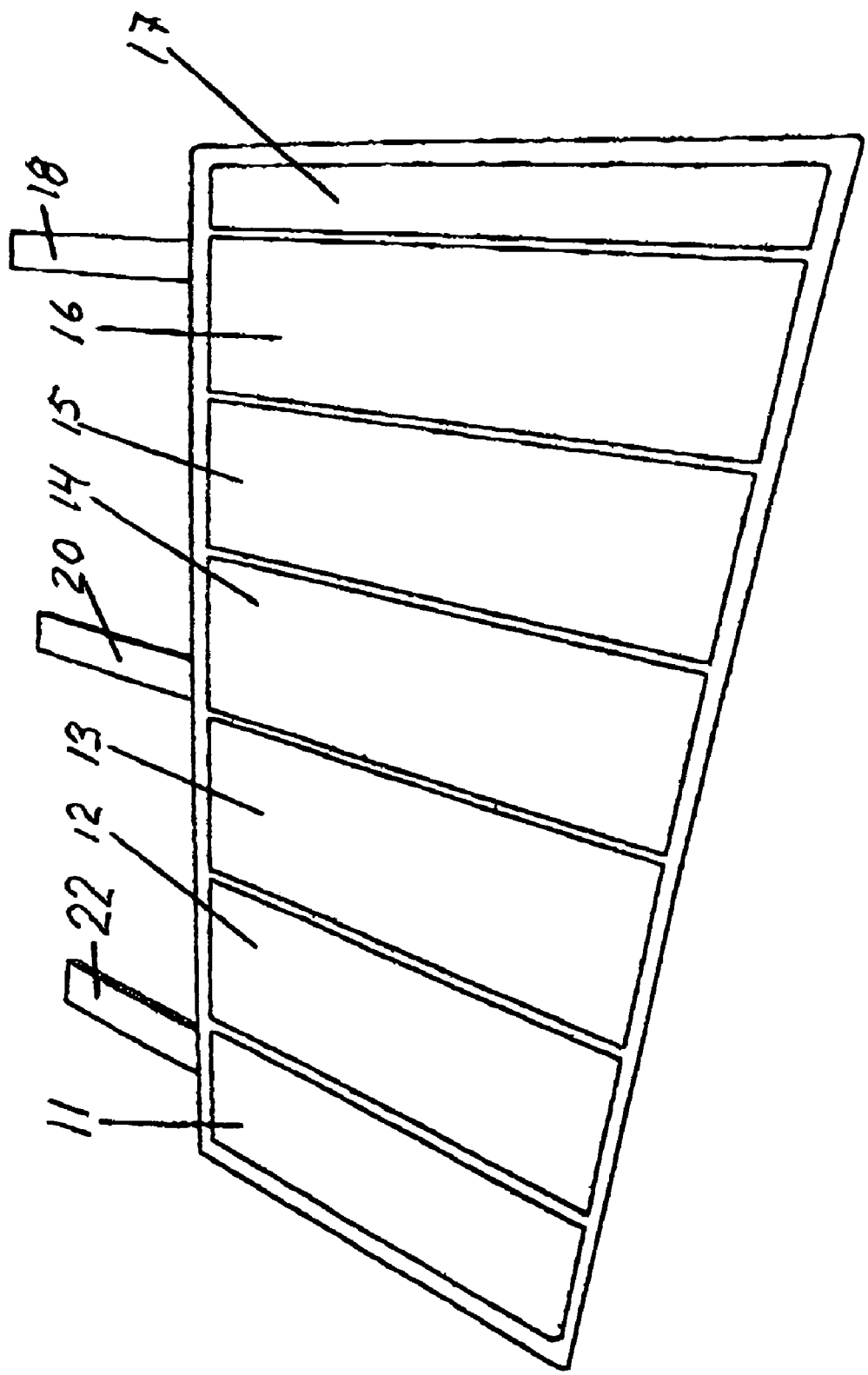

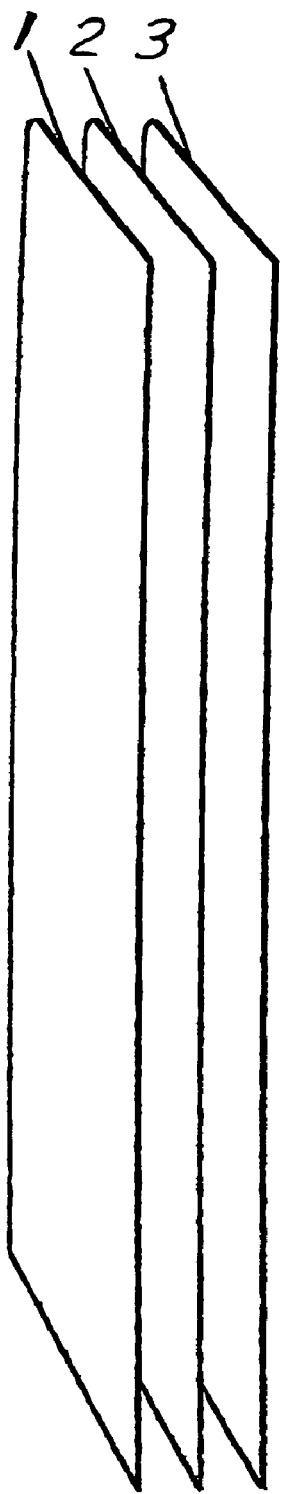
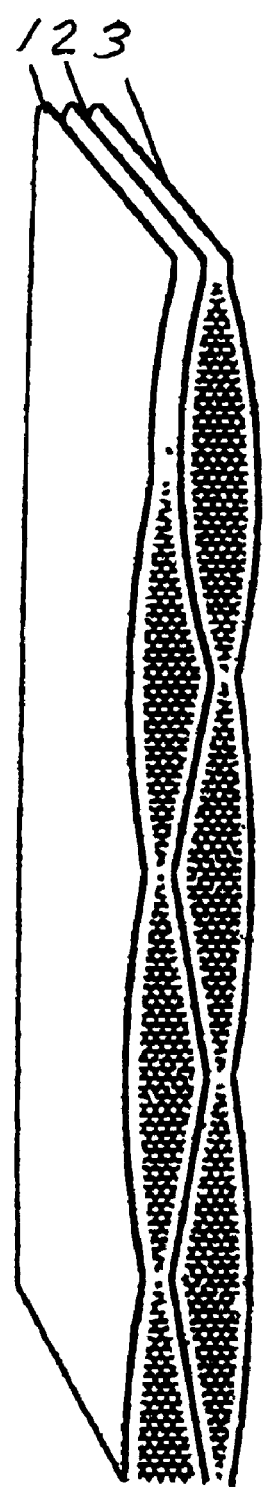
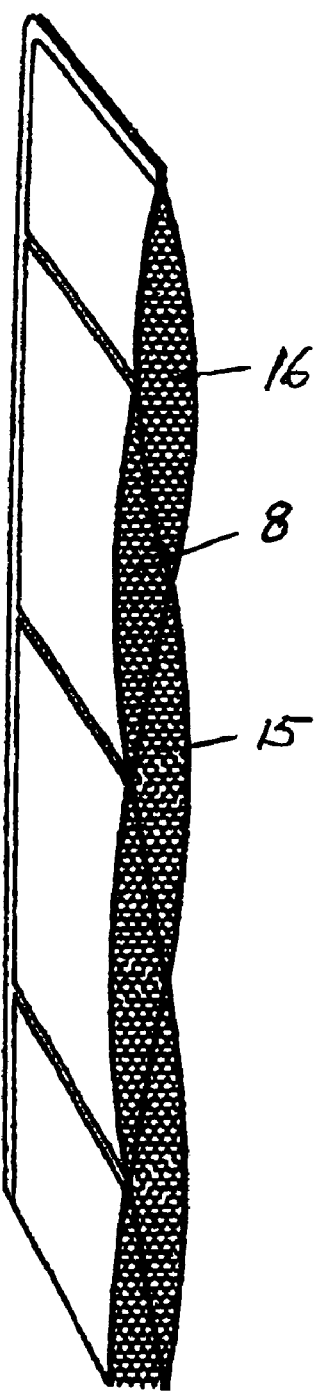

FORMABLE LAMINATE OF ANY CIRCUMFERENCE

FIELD OF THE INVENTION

The present invention is primarily of use in the area of support dressings. As a rule, such dressings are used for bone fractures and other avulsions. Bandages treated with plaster of Paris are used in both these cases. Applying such a support dressing is very messy and, furthermore, it takes some time for the dressing to set. Using a laminate, the previously mentioned disadvantages can be eliminated.

BACKGROUND OF THE INVENTION

It has proved appropriate to use a laminate comprising a number of layers. The two outside layers must not be pervious to gaseous media. The inner layers, on the other hand, must be pervious to gaseous media. As a rule, three layers are sufficient. Of these layers, the outside two are not pervious to gases while the intermediary one does allow gases to pass through. Making use of the intermediary layer and one of the outside layers, a number of sealed compartments are formed, the peripheries of which are created by bonding or welding. Making use of the other outside layer, a number of compartments are formed and oriented in such a way that each of these compartments is connected, via the intermediary layer, to two of the compartments formed by the intermediary layer and the first outside layer. One of the two outside layers has a valve. Through this and the intermediary layer, a vacuum pump can connect to, and set up a total vacuum in, all the compartments. All the compartments are wholly or partially filled with a packing material. Granulates make a suitable filling/packing material.

The formable laminate can, for example, be applied to an arm and more or less completely encircle the limb. Once in position, a vacuum generator is attached and a complete vacuum set up in all the compartments. This renders the laminate as stiff as a plaster of Paris dressing. The laminate can also have fasteners of some description at its outer edges. Using the fasteners, a laminate wrapped around an arm can be fixed in such a way that it remains in position on the object for which it is to form a support dressing when a vacuum is set up in the laminate. If the material and valve are made of first-class materials, a support dressing constructed from a laminate as per the present invention can have a service life equal to that of a plaster of Paris dressing. Said valve is of such a design that it can also release the vacuum. Consequently, the laminate as per the present invention can be used several times, this reducing the costs involved in applying various support dressings. It has proven possible to use polyurethane for the outside layers and a permeable material for the intermediary layer. Polypropylene is suitable for the filling material. However, it is presumably clear that, provided the laminate can be brought from a formable to a rigid condition, a large number of materials are suitable for the layers and filling.

In the foregoing, it has been intimated that the laminate is suitable for medical care purposes. It is intended that the laminate can, in this connection, be amongst the equipment carried by ambulances. If necessary, it can also be kept available as a useful aid at other places, for example, ski slopes. In this latter instance, it could be used as a first support dressing for fractures, it being intended that the laminate should be replaced by a different support dressing at the hospital. However, it is also possible that a support dressing of the same sort could be used at the hospital.

The laminate can be produced for sale as an item sold by the meter, each unit then having its own valve. It may be appropriate to arrange the compartments side by side on each side of an intermediary layer. With such an arrangement, it is particularly appropriate to have the compartments parallel with each other and, preferably, straight.

A laminate as per the present invention can have a rectangular design and be of such dimensions that a person could be placed on the laminate. If a laminate of this design has some form of handle in each of its four corners, and is also equipped with a valve that allows for the setting up of a vacuum, then a stretcher can be easily created.

The laminate can be used to create boarding appropriate for covering various openings in properties. It is similarly possible to make lids for barrels and seal off openings in pipework.

The advantage of a laminate as per the present invention is that, in its formable state, it can be used to create any sort of body, which, when a vacuum is set up, can remain in the desired position.

As per the present invention, the laminate can thus be made up of two outside layers that are impervious to gaseous media and a number of intermediary layers, which have to be pervious to gaseous media. In this way, a large number of compartments care be created, FIG. 4. When a vacuum is set up in these, a rigid laminate is formed.

Other characteristics of the present invention are contained in the patent claims below.

BRIEF DESCRIPTION OF THE DRAWINGS

An example of the use of a laminate (as per the present invention) intended to serve as a support dressing is described in connection with an examination of the three attached drawings where;

FIG. 1 shows a four-sided laminate viewed from one side,

FIG. 2 shows the four-sided laminate viewed from the other side, and

FIG. 3 shows a three-layered laminate before compartmentalization.

FIG. 4 shows a cross section of the laminate shown in FIGS. 1 and 2.

FIG. 5 shows the laminate shown in FIG. 4 with compartments created by welding or bonding.

DETAILED DESCRIPTION OF THE INVENTION

Looking first at FIG. 3, it is plain and clear that the support dressing is built up of 3 layers (1-3). Layers 1 and 3 are of a material that does not allow gaseous media to pass through. The layer designated as 2 in this figure is, on the other hand, of a material that does allow gaseous media to pass through. Layers 1 and 2 are used to create a number of compartments (4-10 in FIG. 1). The edges of these compartments are joined to each other to create pockets for a filler. This can be a granulate, for example polypropylene or any other material with similar properties. The bottom of every such compartment formed by layer 2 is pervious to gaseous media. Provided that it allows gaseous media to pass through, layer 2 can be made of any suitable material whatsoever. Both outside layers may appropriately be made of polyurethane or of any other material that has the same properties. Instead of using a granulate, other fillers having the same properties as a granulate can be used. Thus, materials with fluid or semi-fluid consistencies can be considered. Making use of the intermediary layer (2) and the other outside layer (3), compartments are created by circumferential sealing effected by welding or bonding, FIG. 5. Via the intermediary layer (2), these compartments are so arranged that each of them is connected to two compartments on the other side of said layer. Thus, in FIG. 5, compartment 8 is connected to compartments 15 and 16. The laminate, which has four sides (25-28 in FIG. 2), is equipped with fasteners. In the present case, these can be Velcro strips and, in FIG. 2, they have been given the identifying numbers 18-23.

The laminate shown in FIG. 1 can be used, for example, to wrap around an arm in which a bone has fractured. When wrapping has finished, the laminate can be fixed in place by bringing the Velcro strips into contact with each other. When this has been done, the valve (24) is used to set up a vacuum inside the laminate. This renders the laminate rigid. Easily, extremely quickly and without any mess, the laminate is now functioning exactly as a plaster of Paris dressing.

If it is made to an appropriate size, a rectangular laminate such as that illustrated in FIG. 1 can also be used as a stretcher. In this case, the laminate should have some form of handle in each of its four corners. A rectangular laminate can even be used as a wall element for covering undesired openings. Furthermore, a laminate as per the present invention can be given any shape whatsoever. By taking the laminate to its rigid condition, a rigid shape is then achieved.

It is clear that the laminate as per the present invention has a good number of uses that are not restricted to medical care alone, but extend to all situations needing a formable laminate capable of being brought to a rigid condition when the required form has been established.

The filling material in each compartment must be of such a nature that it becomes rigid when a vacuum is set up. A wide range of materials satisfying this requirement can be considered. As regards the two types of layer, namely, pervious to gaseous media and impervious to gaseous media, all types of materials having these properties can be used. The use of plastic foils, metal foils and rubber products is imaginable.

The invention claimed is:

1. A laminate comprising:
a first outside layer having an inner surface;
a second outside layer having an inner surface; and
an intermediate layer disposed between said first and second outside layers, said intermediate layer having opposed first and second surfaces;
wherein said intermediate layer is pervious to gaseous media;
wherein said first and second outside layers are impervious to gaseous media;
wherein said first and second surfaces of said intermediate layer are connected to said inner surfaces of said first and second outside layers at alternating points to create compartments between said outside layers and said intermediate layer;
wherein each compartment is partially or wholly filled with a filling material;
wherein each compartment on each side of the intermediate layer has, through a common interface with the intermediate layer, contact with two compartments on the opposing side of the intermediate layer;
wherein the compartments are heat sealed; and
wherein either one of the first and second outside layers has a valve assembly to allow a vacuum to be set up and maintained in each compartment.

2. A laminate according to claim 1, wherein each compartment is formed by two adjacent layers, the periphery of the compartment having the two layers joined so that the compartment is sealed.

3. A laminate according to claim 1, wherein the compartments on each side of an intermediate layer are arranged side by side.

4. A laminate according to claim 1, wherein the first and second outside layers are made of plastic or rubber.

5. A laminate according to claim 1, wherein the compartment filling material becomes rigid when subjected to a vacuum.

6. A laminate according to claim 1, wherein the laminate is of rectangular dimension.

7. A laminate according to claim 1, wherein the laminate is of four-sided dimension, two opposing sides having fasteners that allow these two sides to be fastened to each other.

8. A laminate comprising:
a first outside layer having an inner surface;
a second outside layer having an inner surface; and
an intermediate layer disposed between said first and second outside layers, said intermediate layer having opposed first and second surfaces;
wherein said intermediate layer is pervious to gaseous media;
wherein said first and second outside layers are impervious to gaseous media;
wherein said first and second surfaces of said intermediate layer are connected to said inner surfaces of said first and second outside layers at alternating points to create compartments between said outside layers and said intermediate layer;
wherein each compartment is partially or wholly filled with a filling material;
wherein each compartment on each side of the intermediate layer has, through a common interface with the intermediate layer, contact with two compartments on the opposing side of the intermediate layer;
wherein the compartments are heat sealed; and
wherein the compartment filling material becomes rigid when subjected to a vacuum.

9. A laminate according to claim 8, wherein each compartment is formed by two adjacent layers, the periphery of the compartment having the two layers joined so that the compartment is sealed.

10. A laminate according to claim 8, wherein the compartments on each side of an intermediate layer are arranged side by side.

11. A laminate according to claim 8, wherein either one of the first and second outside layers has a valve assembly to allow a vacuum to be set up and maintained in each compartment.

12. A laminate according to claim 8, wherein the first and second outside layers are made of plastic or rubber.

13. A laminate according to claim 8, wherein the laminate is of rectangular dimension.

14. A laminate according to claim 8, wherein the laminate is of four-sided dimension, two opposing sides having fasteners that allow these two sides to be fastened to each other.

* * * * *